US005831034A

United States Patent [19]
Katinger et al.

[11] Patent Number: 5,831,034
[45] Date of Patent: Nov. 3, 1998

[54] HUMAN MONOCLONAL ANTI-HIV-I-ANTIBODIES

[75] Inventors: Hermann Katinger, Heiligenstadterstrasse 131-139, A-1190 Vienna; Alois Jungbauer, Vienna; Franz Steindl, Vienna; Andrea Buchacher, Vienna, all of Austria

[73] Assignee: Hermann Katinger, Austria

[21] Appl. No.: 293,842

[22] Filed: Aug. 22, 1994

Related U.S. Application Data

[63] Continuation of Ser. No. 693,730, Apr. 30, 1991, abandoned, which is a continuation-in-part of Ser. No. 120,489, Nov. 13, 1987, abandoned.

[51] Int. Cl.⁶ .............................. C07K 16/00; C12Q 1/70; C12P 21/06; A23J 1/00
[52] U.S. Cl. ........................ 530/388.35; 435/5; 435/69.1; 530/413; 536/23.53; 536/24.2
[58] Field of Search ................... 435/5, 69.1; 536/23.53, 536/24.2

[56] References Cited

U.S. PATENT DOCUMENTS 5,087,557  2/1992  McClure ...................................... 435/5

OTHER PUBLICATIONS

Fahey, et al., Status of immune-based therapies in HIV infection and AIDS, Clin. exp. Immunol., 88, 1–5, see p. 3, second column, third full paragraph, Jan. 1992.

Primary Examiner—Ponnathapura Achutamurthy
Assistant Examiner—Hankyel T. Park
Attorney, Agent, or Firm—Bierman, Muserlian and Lucas

[57] ABSTRACT

Novel human monoclonal anti-HIV-I antibodies and immunochemicals made from the antibodies and method of treating or preventing HIV-I infections.

4 Claims, 6 Drawing Sheets

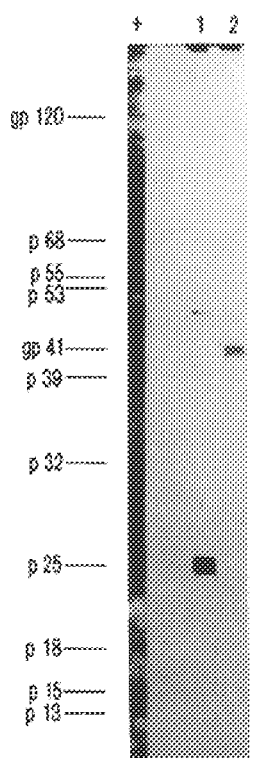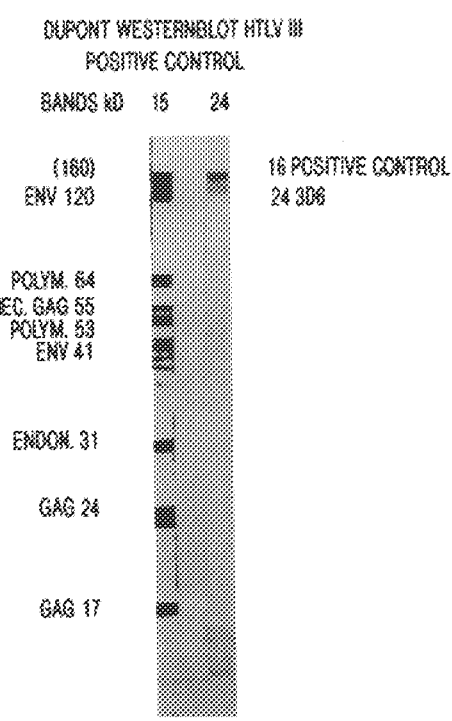
FIG. 1a   FIG. 1b   FIG. 1c

HUMAN MONOCLONAL ANTI-HIV-I-ANTIBODIES

This application is a continuation of U.S. patent application Ser. No. 07/693,130, filed Apr. 30, 1991, now abandoned, which is a continuation-in-part of U.S. patent application Ser. No. 07/120,489 filed Nov. 13, 1987, now abandoned.

This invention is in the field of immunology, specially AIDS therapy and in vivo imaging of HIV-infected cells. More particularly, it concerns human monoclonal anti-HIV-I-antibodies and immunochemicals made from these antibodies and therapeutic methods that use these immunochemicals. The production of human monoclonal antibodies (hu mAbs) may present a new source of antibodies to be used in immunotherapy for infections and other diseases.

The application of mAb of human origin instead of murine origin avoids the induction of antibody response in humans. The Fc-part of murine antibodies has to be removed prior to injection in humans to minimize antibody response against heterogenous administered proteins. Human monoclonal antibodies however present a part of the homologous proteins of human individuals.

In the sera of human immunodeficiency virus (HIV) infected men, anti-virus antibodies could be detected over a certain period after infection without any clinical manifestations of the acquired immunodeficiency syndrome (AIDS). At this state of active immune response, high numbers of antigen-specific B-cells were expected in the circulation. These B-cells were used as fusion partners for the generation of human monoclonal anti HIV antibodies.

We describe here:

the generation of human mAb to HIV antigens the substantial inhibition of growth of HIV-infected cells the preparation of immunotoxins conjugated with the described human anti-HIV-mAb and an A-chain toxin the selective killing of HIV-I infected cells with the immunotoxin -the selective killing of HIV-I infected cells by antibody dependent cellular cytotoxicity the selective prevention of infection of cells with the human monoclonal anti-HIV-I antibody In the presently preferred embodiment of the invention, the human anti-HIV-I-mAb used is of $IgG_1$ subclass produced by known hybridization procedures described by R. Kennet et al. in "Monoclonal antibodies and functional cell lines; progress and applications". Plenum Press (New York), 1984.

Samples of hybridoma 3D6 were deposited in ECACC, Portion Down, Salisbury SP4 OJG, UK. 3D6 was one of the six hybridomas that produce antibodies recognizing HIV-envelope proteins in parent application Ser. No. 120,489. The ECACC accession number and deposit date for the deposited hybridoma is: 87110301; 3rd Nov. 1987. The following antibodies were deposited at the same depository on Sep. 17, 1990 under the following accession numbers.

| Antibody | Accession No. |
| --- | --- |
| 3A6 | 90091701 |
| 24G3 | 90091702 |
| 4E10 | 90091703 |
| 2F5 | 90091704 |
| 4D4 | 90091705 |
| 1F11 | 90091706 |
| 37G12 | 90091707 |
| 1H5 | 90091708 |
| 4G2 | 90091709 |

FUSION

Fusion was performed in a described manner (Kohler et al., Europe Journal of Immunology 6 (1976): 292). Prior to cell fusion with PEG 1500, peripherial blood lymphocytes from HIV I serum positive donors were washed 3 times with serum free cell culture medium. The cells were fused immediately or stimulated with 5 ng pokeweed mitogen (PWM) for three days prior to fusion. The cells were mixed at a ratio of 5:1 with HAT-sensitive fusion cells. The cells were fused with 42% PEG (2500 Ferak, FRG) in the presence of 7.5% DMSO (Serva, FRG). Cells were cloned and subcloned by limiting dilution.

SCREENING OF THE HYBRIDOMAS

IgG and IgM isotypes were analyzed from the culture supernatant by a sandwich enzyme linked immunosorbant assay (ELISA) with peroxidase conjugated anti human IgG, IgM (heavy chain specific) antibodies in a known manner. Screening for specific antibodies was performed by a sandwich ELISA using HIV in a concentration of 10 microgram/ml. The virus isolated from tissue culture was coated in flat bottom microtiterplates and the unbound material was washed out. The culture supernatants were incubated overnight at 4° C. After washing out unbound material, the specific antibodies were detected by anti human-Ig-heavy-chain specific antibodies labelled with peroxidase.

IMMUNOBLOTTING

Immunoblot using HIV envelope proteins prepared from native virons: Purified virus was denaturated and reduced with 2.5% SDS and 5.0% 2-mercaptoethanol at 90° C. for 5 minutes and applied to a 10% polyacrylamide slab gel. After separation, protein bands were electro-transferred into a nitro-cellulose sheet (Schleicher & Schull, FRG). After blocking the sheet with 5% dry milk, strips were cut and immersed in 5 ml 1:2 diluted culture supernatant. Bound antibodies were detected by reacting with anti-human IgG antibodies labelled with HRP and staining with diaminobenzidine containing 0.1% $NiCl_2$.

IMMUNOBLOT USING HIV ENVELOPE PROTEINS PREPARED FROM CLONED MATERIAL

SDS-gel electrophoresis was performed according to Laemmli, Nature, Vol. 227, 1970; p 680–685. The electrophoretically separated envelope proteins derived from genetically engineered E. coli (L. H. gosting, et al.: Journal of Clinical Microbiology 25; 1987 (845–848)), were electro blotted to nitrocellulose. After blocking with 3% bovine serum albumin (BSA dissolved in PBS), the strips were immersed in samples diluted in PBS buffer (containing 0.1% Triton X-100, 1% BSA, 0.5% gelatin) overnight, washed 3 times and incubated with goat anti-human GAMMA-chain labelled with peroxidase.

Immunoblots using commercial available blot strips

Blot strips from Du Pont Lot 7044128 were used according to recommendations of the company.

HYBRIDIZATION DETECTION OF HUMAN DNA $10^6$ cells of each cell line were spotted on a nitrocellulose membrane. The hybridization probe was the $^{32}$P-labelled plasmid pBlur8 which contains a cloned Alu-sequence that is specific for human DNA and repeated about 300,000 times in the genome (Schmid et al., Science 216 (1982):1065).

After prehybridization and hybridization overnight, the membrane was washed 3×100, ml 2×SSC, 0.1% SDS for 5 minutes at room temperature and 2×in 200 ml, 1×SSC, 0.1% SDS for 30 minutes at 60° C and autoradiographed for 80 hours.

IMMUNOFLUORESCENCE

Fixed HIV-I infected cells (H9 cells) were incubated with the hu anti-HIV-mAb. Binding of the mAb was demonstrated by a second incubation after washing out, unbound mAb with FITC labelled anti human IgG.

PURIFICATION OF THE 3D6-ANTIBODIES

Purification was performed in a known manner. The clarified culture supernatant was desalted using gel filtration on Sephadex G-25 column (Pharmacia) and further chromatographed on a CM-Sepharose fast flow column (Pharmacia). The eluate of the CM-Sepharose fast flow column was concentrated by ultra-filtration and rechromatographed using Phenyl-superose (Pharmacia). The chromatographic steps were performed according to the recommendation of the Pharmacia company. Prior to the loading of the solution on the Phenyl-superose column, the crude mAb solution was diluted by a 2M-ammonium sulfate solution.

PREPARATION OF RICIN-A-CHAIN TOXIN

Extraction of Ricin from the castor bean

Ricin is extracted from castor beans (*Ricinus communis*) by known methods. Ricin is extracted either from ground whole castor beans (*Ricinus communis*) or from castor bean cake, which is a by-product of castor bean processing. The castor bean cake is defatted by extraction 3 times with 5 volumes of (v/w) 40% to 60% petroleum ether. The air-dried material is then extracted overnight in phosphate buffered saline (PBS; 0.15M NaCl, 0.01M phosphate, pH 7.2). The extract is cleared by filtration through a nylon gauze followed by centrifugation at 1500 g for 1 hour. The clear supernatant is precipitated at 4° C. with saturated ammonium sulfate. At a final end concentration of 60% ammonium sulfate, the precipitate is collected and harvested by centrifugation (1500 g, 1 hour), redissolved in a minimum amount of PBS and dialyzed against PBS until the extract is ammonium sulfate free.

CLEAVAGE OF RICIN INTO A- AND B-CHAIN

The affinity purified and concentrated toxin is cleaved into A- and B-chain by a 5% -mercapto ethanol solution. The toxin is incubated at a concentration of 5 mg/ml in 0.1M Tris-HCl pH 8.5 buffer completed with -mercapto ethanol (5% end concentration) and galactose (0.5M end concentration) overnight at room temperature, followed by 2–3 hours at 37° C. The toxin is transferred from the starting buffer (PBS) into the incubation buffer (Tris buffer) by gel chromatography on Sephadex G25 columns equilibrated with the incubation buffer.

After incubation, the sample is applied to a DEAE-Sepharose fast flow equilibrated with 0.1M Tris/HCl buffer pH 8.5. The column is washed with 0.1M Tris/HCl buffer 8.5 until all unbound material is eluted. The unbound material, essentially pure A-chain, is collected and passed down an asialo-fetuin-Sepharose 4B column to remove contaminating toxin. The asialo fetuin-Sepharose 4B was prepared according to the recommendation of Pharmacia company. The unbound material is collected and filter sterilized and stored at 4° C. The DEAE-Sepharose fast flow is regenerated with a 0.1M Tris-HCl pH 8.5 containing 0.1M Galactose and 1 M NaCl.

AFFINITY CHROMATOGRAPHY

The clarified and dialyzed toxin extract is further purified by lectin affinity chromatography. The gel (Sepharose 4B, Fa. Pharmacia) is pretreated with 1M propionic acid at room temperature for at least 4 weeks to enhance its binding capacity for lectins. The column chromatography should be operated at temperatures lower than 10° C. to optimize lectin binding. The clarified and dialyzed extract is applied to a PBS equilibrated acid pretreated Sepharose 4B-column. After sample application, the column is washed with PBS until the UV-absorbance return to the baseline. The toxin is eluted together with other lectins with 100 mM galactose in PBS. This mixture is further separated by gel-chromatography on Sephacryl S200HR. The sample volume should not exceed 3–4% of the bed total volume. The toxin is resolved completely from the other lectins under these conditions.. The toxin recovered from the affinity column is concentrated to 10 mg/ml by ultrafiltration (Millipore PTGC membrane) prior to application on the Sephacryl S200 HR column.

The toxin peak was collected and filter sterilized. The sterile toxin solution was stored deep frozen at −30° C. until cleavage into A and B-chain.

DETERMINATION OF THE ISOELECTRIC POINT

The isoelectric point of the hu anti-HIV-I-mAb was determined by a described method. Pharmalytes were used as carrier ampholytes. The whole procedure was carried out according to the recommendation of the Pharmacia company (booklet: Isoelectric focusing, Pharmacia fine chemicals).

DETERMINATION OF SUBCLASS AND LIGHT CHAINS

Light chains and subclass were determined by ELISA. Specific anti human Kappa-chain antibodies labelled with alkaline phosphatase or specific anti human $G_1$, $G_2$, $G_3$ and $G_4$ antibodies labelled with peroxidase were used.

QUALITY CONTROL OF RICIN A-CHAIN

Quality control tests are performed on the purified Richin-A chain. Gradient SDS-polyacrylamide gel electrophoresis under reduced conditions shows the absence of any contaminating material. Only one band at 33 and one at 30 kilodalton respectively can be detected.

CONJUGATION OF A-CHAIN TOXIN WITH MONOCLONAL ANTIBODY 5 mg of purified monoclonal antibody (1–2 mg/ml in PBS) were reacted with a 10-fold molar excess of SPDP (Pharmacia), dissolved at 1 mg/ml in dimethylformamide for 30 min at room temperature. PDP-substituted antibody was desalted by gel filtration using Sephadex G-25. The protein peak as determined continuously at 280 nm was collected and placed on ice. Five mg of ricin A chain were reduced with 5 mM DDT for 1 hour at room temperature and desalted on a column of Sephadex G-25. The column was equilibrated with PBS. The protein peak was collected and was immediately mixed with the cold PDP-substituted antibody. The mixture was rocked for 1 hour at 4° C. and then diafiltrated at 4° C. against 0.01M sodium phosphate buffer containing 2.0 sodium chloride. The bulk of the unconjugated A-chain was separated from the immunotoxin by gel chromatography on Sephacryl S200 HR. The column was equilibrated in 0.02M sodium phosphate containing 3M sodium chloride.

The first peak, which contained the immunotoxin was pooled and the affinity purified on an anti-human IgG-Sepharose 4B. The immunotoxin was eluted from the affinity column with 3.5M magnesium chloride and extensively dialyzed against sodium chloride and then against PBS.

Immunotoxins (0.2–2 mg/ml) were concentrated by ultrafiltraion using PTCC membranes to the end concentration necessary for testing. The final preparation was sterile filtered and stored in aliquots at −20° C. The immunotoxins were analyzed by SDS-PAGE under both reducing and nonreducing conditions. The substitution of the immunotoxin was determined by radioimmunoassay. An average substitution of 1–2 moles A-chain per mole antibody was observed.

COMPETITIVE EIA

Purified hu anti-HIV-mAb were conjugated with Peroxidase by a known method according to M. B. Wilson and P. K. Nakane (1978) in "Immunoflourescence and related techniques" ed. W. Knapp et al. Elsevier, Netherlands.

A dilution series of hu anti-HIV-mAb (in PBS 1% BSA and 0.1% Triton X-100) was dispensed in flat bottomed microtiter wells coated with purified HIV envelope proteins incubated overnight at 4° C. After washing out unbound material, the bound conjugate was determined by reaction with 1,4 phenylenediamine. The developed color was measured at 492 nm. A calibration curve was blotted optical density versus dilution. The dilution of the half saturation is calculated from this calibration curve.

Hu anti-HIV-mAb at a dilution corresponding to the half maximum saturation was mixed with sera from patients suffering from AIDS or with sera from probands who were sero positive determined by a conventional screening (ELISA) followed by a confirmation test (westernblot). The mixture of the conjugate (at half maximal dilution) and the serum from the probands were incubated in HIV envelope protein coated microtiter wells, washed and stained. The optical density of these samples is compared to the anti-HIV-mAb at half maximum saturation. A value below the half maximum saturation indicates a competition between the human sera and the human monoclonal anti-HIV antibody.

NEUTRALIZING ACTIVITY ON THE INFECTIVITY OF HIV-I VIRIONS

The assay for neutralizing activity of the hu anti-HIV-I-mAb was performed according to a knowm method (J. Virology, Vol. 61, p 2024–2028,1987), Nature, Vol. 316, p 72–74, 1985; Biotechnology, Vol. 5, p 940–946, 1987).

An HIV-I dose equivalent to twenty times the amount to cause infection in 50% inoculated cultures on day 12 (20× $TCID_{50}$) was used to infect the H9-cell line. Cells were collected 3, 6, 9 and 12 days after virus inoculation and percentage of infection was determined by immunfluorescence. 100% infection was observed between day 6 and 9. The neutralizing effect was also tested in the presence of the monoclonal antibody at variable dilutions.

CYTOTOXICITY TESTS

The test cell line used in the cytotoxicity tests were HIV-I infected H9 cells. HIV-I infected H9 cells were prepared as described under Neutralizing activity on the infectivity of HIV-I virons. Uninfected H9 cells were used as negative control. Cells harvested after a period of 6 to 9 days after virus inoculation were suspended in 1 ml medium. Various dilutions of the hu mAb-toxin conjugate were added to the infected cells and the negative control. After incubation for 24 hours at 37° C., cells were washed with PBS and methionine free medium supplemented with $^{35}$S-methionine was added. Cells were incubated for 2 hours at 37° C., then the medium was removed by centrifugation and the cells transferred to a glass fiber filter and washed three times with 10% trichloroacetic acid, containing 1 mg/ml methionine. The cells were air dried on the filter and then transferred into a scintillation fluid. Radioactivity was counted in a scintillation counter. Cytotoxicity was expressed as the tissue culture inhibitory dose of the conjugate that resulted in 50% of control untreated protein synthesis ($TCID_{50}$)

EXPERIMENTAL RESULTS

A variety of experiments are shown to serve as examples for illustrating the present invention and its utilization in the following embodiments. The human origin, the biochemical properties, the immunochemical characterization, the in vitro and in vivo behaviour are demonstrated by representative results.

GENERATION OF CLONES AND HUMAN ORIGIN OF THE MONOCLONAL ANTIBODIES

A variety of clones was obtained by the fusion of peripheral blood lymphocytes and the fusion cell line. The specificity of 6 hybridomas is shown in Table I.

TABLE I

Characterization of 6 hybridomas

| Hybridoma No. | Specifity of mAb test by immunoblotting | isotype and subclass | light chain |
|---|---|---|---|
| 3D6 | gp41, gp120 | G | KAPPA |
| 3D9 | gp41 | G | n.d. |
| 24G3 | gp160 | G | n.d. |
| 25C2 | gp120 | G | n.d. |
| 54E7 | gp41, gp160 | M | n.d. |
| 81C7 | gp160 | M | n.d. | n.d. = not determined

The hybridoma No 3D6 is deposited in the ECACC, Porton Down, Salisbury, UK under the deposition No. 8711031 (3rd Nov. 1987). The hu mAb anti HIV-I produced by this hybridoma line (3D6) is used as example to illustrate the present invention. Immunoblots of the 3D6 antibody are shown in FIGS. 1a, b and c.

BRIEF DESCRIPTION OF THE DRAWINGS

FIG. 1a is an immunoblot of the human mAb produced by Hybridoma No. 3D6. HIV envelope proteins were prepared from native virons by SDS and 2-mercaptoethanol treatment. The human origin of the monoclonal antibody is shown by the hybridization of 32P-labelled plasmid D Blur8. Autoradiographs are shown in FIG. 2 with the DNA of the hybridoma cells. Also the reaction with anti human IgG and human IgM antisera and the more specific sera for subclass determination verifies the human origin of the monoclonal antibodies.

FIG. 1b is an immunoblot of the human anti HIV-mAb produced by Hybridoma 3D6 HIV envelope proteins prepared from genetically engineered E. coli (according to a known procedure, L. H. Goesting et al., Journal of Clinical Microbiology 25, 1987 (845–848)).

FIG. 1c is an immunoblot of the human anti HIV mAb produced by Hybridome 3D6. A commercially available blot strip (Du Pont Lot: 70 44 128) was used.

BIOCHEMICAL PROPERTIES AND IMMUNOCHEMICAL CHARACTERIZATION OF THE ANTIBODY

The isotype of the monoclonal antibody produced by Hybridoma No. 3D6 is The subclass determined by ELISA is G. The isoelectric point, determined by isoelectric focusing using the Pharmacia system. The immobilize system is in the range of pH 8.6.

IMMUNOFLOURESCENCE

Figure 2:
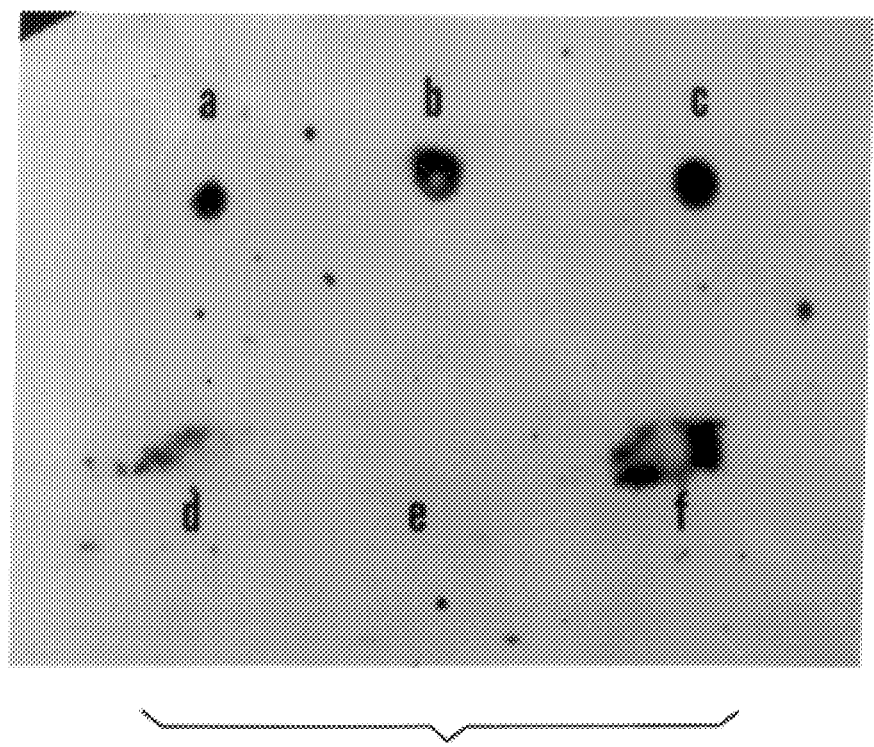
FIG. 2 illustrates the detection of human DNA by hybridization. a) 3D5; b) 3D9; c) 24G3; d) BJA-B (human lymophoid cell line positive control; e) P3X63Ag/653 (murine myeloma negative control; f) BUBTU (human bladder carcinoma positive control).
Figure 3A:
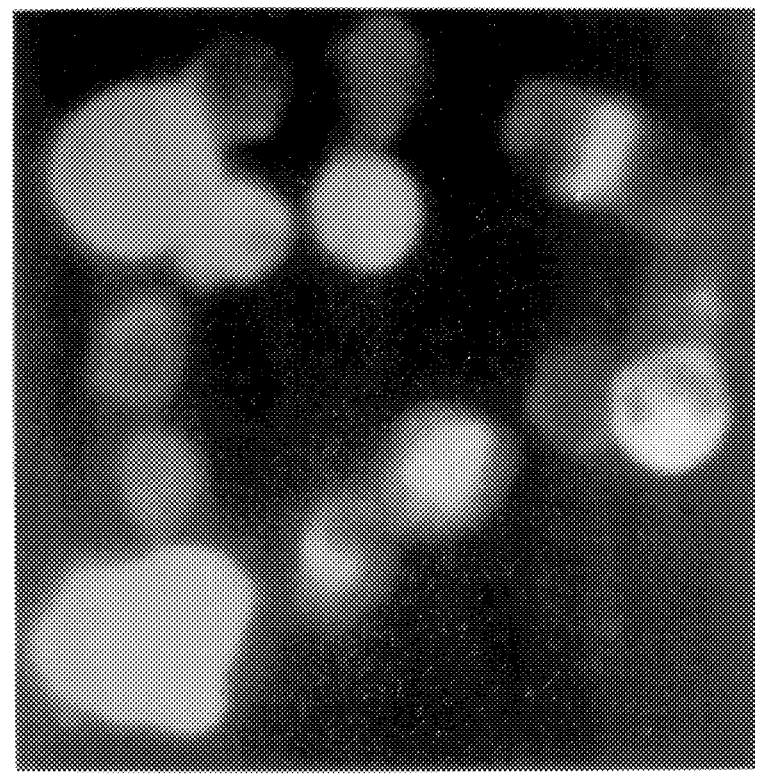
FIGS. 3a and 3b show the immunofluorescence of fixed HIV-I infected H9-cell imaged with a sandwich of 3D6-antibody and anti-human IgG conjugated with FITC.
Figure 3B:
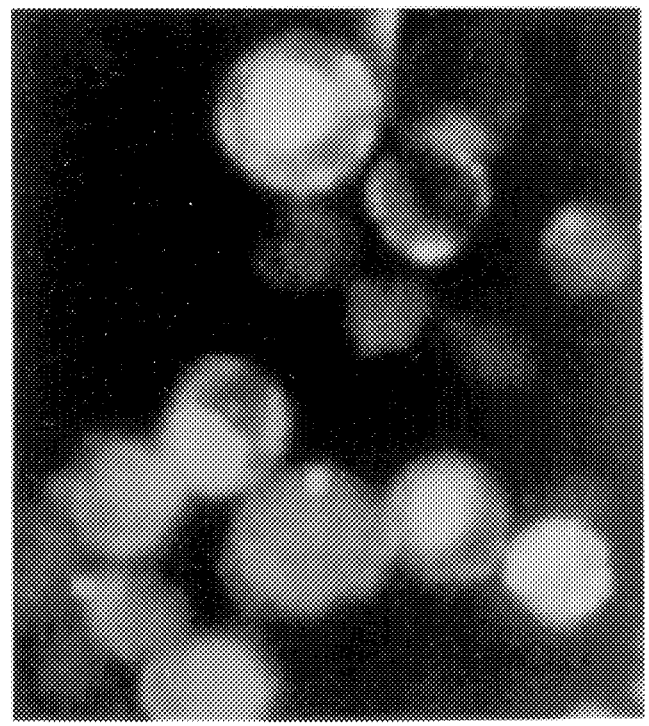

Fixed HIV infected cells were incubated with the 3D6 antibody. Specific flourescene caused by the marker conjugate anti human IgG-FITC is shown in FIG. 3. In FIG. 3 immunoflourescence of fixed HIV-I infected H9-cells imaged with a sandwich of 3D6-antibody and anti human IgG conjugated with FITC. The clone 3D6 and 3D5 is shown.

IN VITRO BEHAVIOUR OF THE MONOCLONAL ANTIBODIES AND RELATED IMMUNOTOXINS

Neutralizing activity

Figure 4:
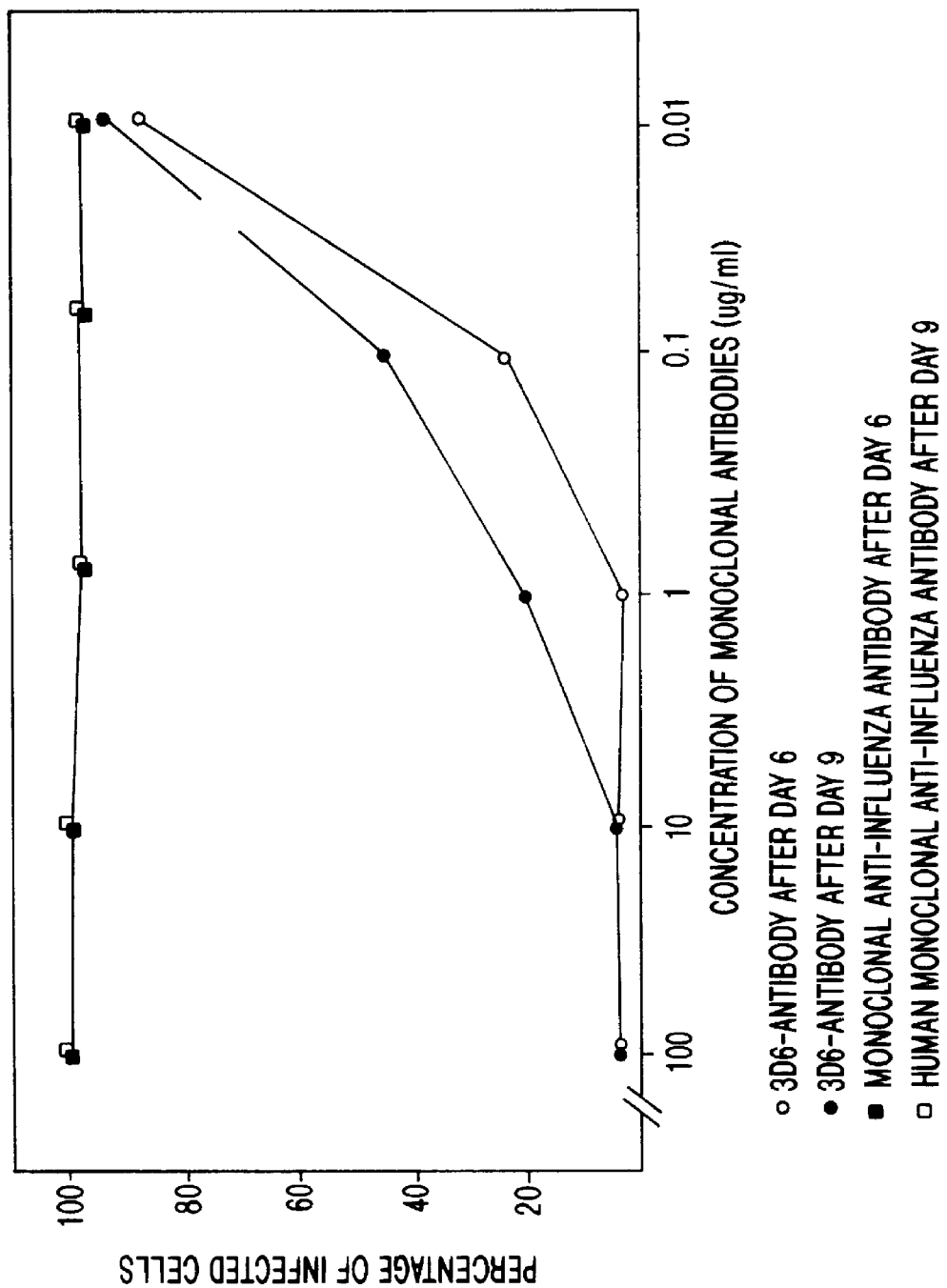
FIG. 4 is a graph illustrating the neutralizing activity of 3D6-antibody expressed as a percent of infected cells.

In the presence of up to 1 ug/ml, 3D6 antibody H9 cells could not be infected by 20 times $TCID_{50}$ of HIV virons. The neutralizing activity is shown in FIG. 4 in which neutralizing activity of 3D6-antibody is expressed as percent of infected cells. Infected cell were shown by immunfluorescence using 3D6 antibody. 9 days after virus inoculation with 20 times TCID 0.1 ug/ml 3D6 antibody could prevent HIV infection in H9 cells.

CYTOXICITY

The monoclonal antibody (3D6) covalently linked with the Ricin-A-chain was used to demonstrate the cytotoxicity of the antibody. The cytotoxicity was measured by $^{35}S$-methionine uptake. The immunotoxin consisting of a conjugate between 3D6 antibody and Ricin-A-chain, prepared as described under materials and methods killed specifically HIV-I infected H9 cells. The $^{35}S$-methionine uptake is expressed in percent of control (FIG. 5).

Figure 5:
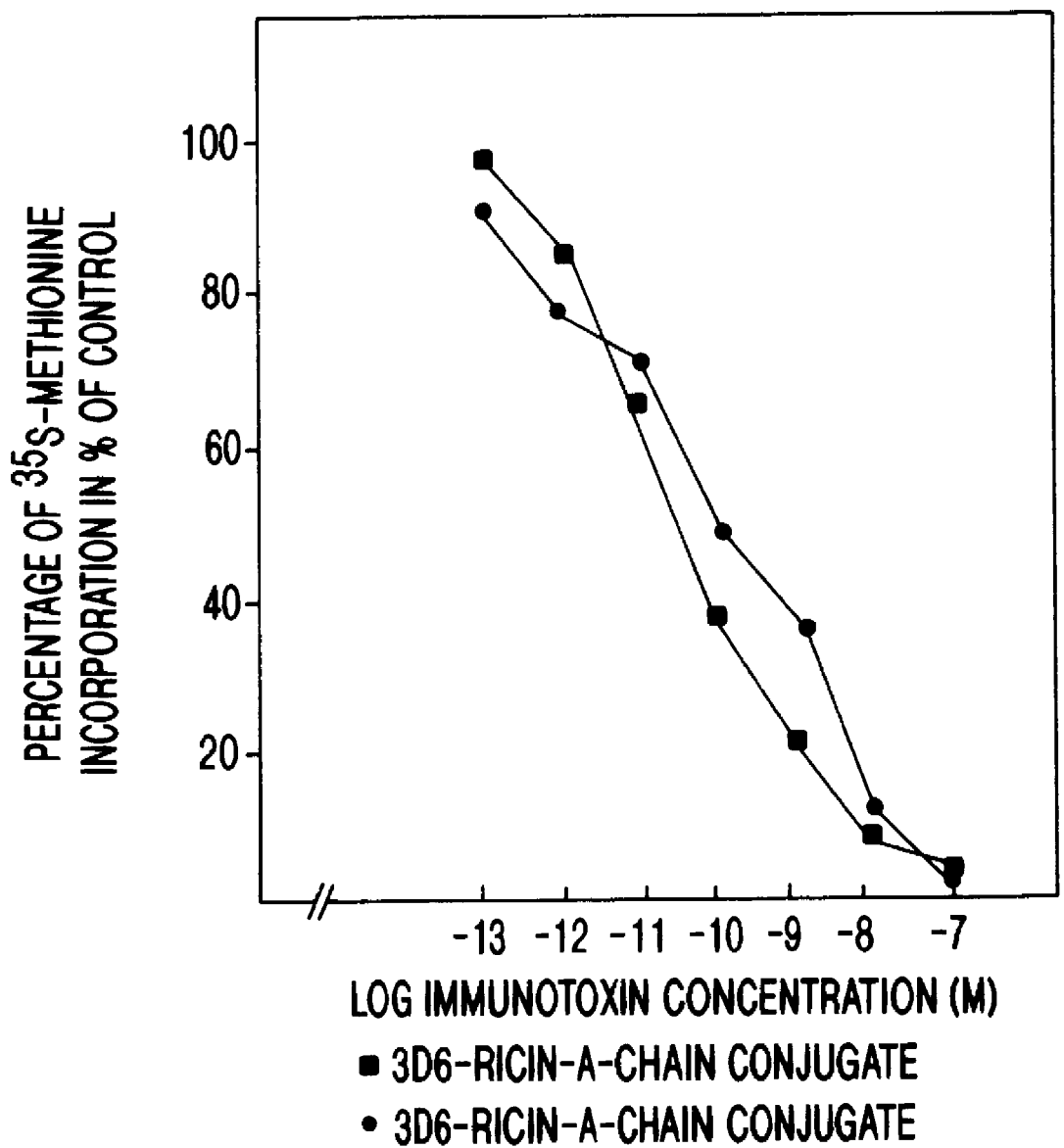
FIG. 5 is a graph illustration $^{35}$S-methionine uptake expressed in a percent of control.
Figure 6:
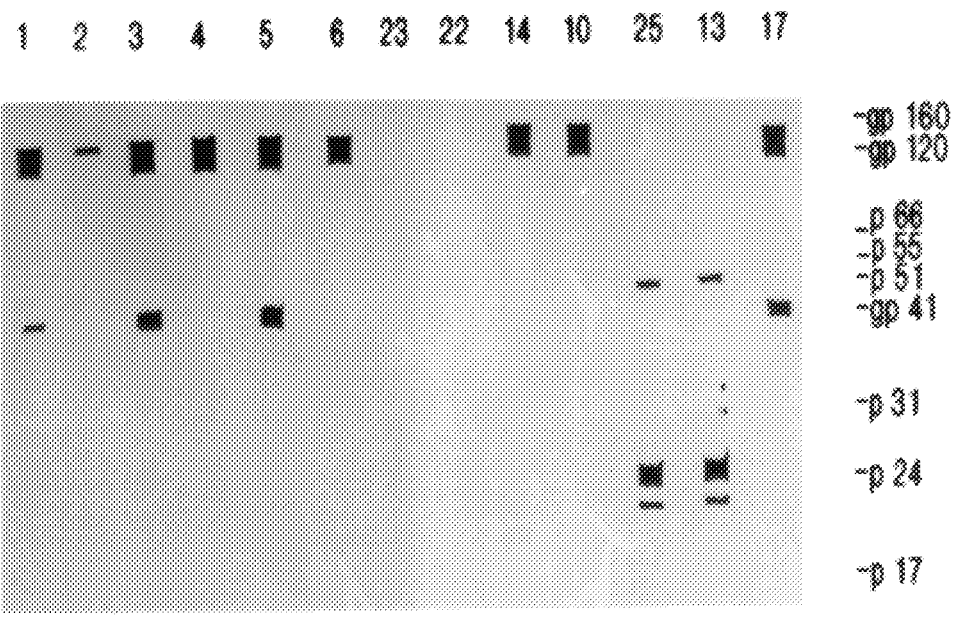
FIG. 6 is the Western Blot test for the test data set forth on page 21 of the application.

FIG. 5 shows inhibition of protein synthesis measured by $^{35}S$-methionine uptake as a measure for cytotoxicity. On the basis of assuming a molecular weight of 180,000 dalton, the molar concentration of the immunotoxin was calculated. The $TCID_{50}$ of the immunotoxin (3D6)-Ricin-A-chain) is less than 10 nm.

COMPARISON OF THE HU ANTI-HIV-mAb WITH NATURALLY OCCURRING ANTIBODIES FROM SEROPOSITIVES AND PATIENTS SUFFERING FROM AIDS OR PRE AIDS

For the comparison of the claimed monoclonal antibodies with naturally occurring antibodies in men after a HIV infection, a competitive EIA (Enzym immunoassay) was chosen. The 3D6 monoclonal antibody was conjugated with Peroxidase and the dilution of the half maximal saturation was determined. The 3D6 antibody at a dilution of half maximal saturation was mixed with different sera from seropositives without clinical manifestation of AIDS and with sera from patients suffering from AIDS or pre AIDS in a ratio of 1:1. The competition between the 3D6 antibody and the natural occurring antibodies in blood are expressed in % of half maximal saturation. The half maximal saturation by the 3D6 antibody is taken as 100%. Table II shows the values from competitive EIA using a 3D6-antibody peroxidase conjugate and different sera.

TABLE II

Comparision between 3D6 antibody and sera from seropositives and patterns suffering from AIDS or pre AIDS.

| Patient No or propand | % Percentage of half maximal saturation | Clinical manifestation of AIDS (1) pre AIDS (2) seropositive proband (3) |
| --- | --- | --- |
| 1 | 96 | 3 |
| 2 | 91 | 3 |
| 3 | 84 | 3 |
| 4 | 88 | 3 |
| 5 | 92 | 3 |
| 6 | 50 | 3 |
| 7 | 94 | 3 |
| 8 | 98 | 3 |
| 9 | 96 | 3 |
| 10 | 85 | 2 |
| 11 | 85 | 3 |
| 12 | 88 | 2 |
| 13 | 95 | 2 |
| 14 | 97 | 2 |
| 15 | 88 | 3 |
| 16 | 88 | 3 |
| 17 | 94 | 3 |
| 18 | 92 | 3 |
| 19 | 96 | 1 |
| 20 | 25 | 3 |
| 21 | 96 | 3 |
| 22 | 94 | 3 |
| 23 | 94 | 3 |
| 24 | 90 | 1 |
| 25 | 82 | 2 |
| 26 | 88 | 3 |
| 27 | 94 | 3 |
| 29 | 94 | 3 |
| 30 | 96 | 1 |
| 31 | 82 | 3 |
| 32 | 86 | 2 |
| 33 | 80 | 3 |
| 34 | 48 | 3 |
| 35 | 84 | 3 |
| 36 | 92 | 3 |
| 37 | 94 | 2 |
| 38 | 98 | 3 |
| 39 | 98 | 3 |
| 40 | 96 | 3 |
| 41 | 88 | 3 |
| 42 | 90 | 3 |
| 43 | 94 | 2 |
| 44 | 92 | 3 |
| 45 | 86 | 3 |
| 46 | 84 | 3 |
| 47 | 92 | 1 |
| 48 | 94 | 3 |
| 49 | 87 | 3 |
| 50 | 96 | 2 |

All sera from all probands were HIV seropositive determined by the conventional screening assay and the seropositivity was confirmed by westernblots. The 3D6 antibody recognizes the same epitopes as naturally occurring antibodies in the blood after HIV infection. In all cases (table II proband 1–50) a competition could be observed.

The established clones are characterized by Westernblots, immunofluourescence using HIV-I positive H9 cells. The subclass of the antibody as well as the class of light chains are also determined and the results are summarized in the following tables and figures.

WESTERN BLOTS

Westernblots were carried out using a HIV-I Westernblot version 1.2 according to the manufacturers protocol (Du Pont de Nemours, Belgium). Purified monoclonal antibodies at a concentration of about 300 ng/ml were tested and the fully developed strip was photographed.

PARTICLE AGGLUTIONATION

A particle agglutination test for screening of antibodies to HIV from Fuijirebio, Tokyo, Japan Serodia-HIV was used. The procedure was carried out according to the manufacturers recommendation. Briefly, the component of reagent of Serodia-HIV is of gelatin particles sensitized with inactivated HIV antigen which was processed by disruption of purified virus with detergent. These sensitized particles were agglutinated by presence of HIV antibodies in serum or plasma or other fluids. All described clones showed positive reaction.

IMMUNOFLUORESCENCE

The immunofluorescence was carried out with H94cells infected with HIV-I (HTLVIIIB). The cells were fixed with methanol and the mixed cells were incubated with an appropriate amount of antibody. The bound antibodies were detected by an FITC labelled anti human IgG F(ab)$_2$ antibody. Negative control was uninfected H9 cells.

ISOELECTRICAL POINT

The isoelectrical point (IEP) was determined by isoelectrical focusing (IEF) using the method described in the Pharmacia IEF manual. The IEP's are listed in the following table.

TABLE 1

Summary of human hybridomas and the corresponding antibodies.

| name | epitop | particle agglut. | subclass light chain | IEP | date* ECACC |
|------|--------|------------------|----------------------|------|-------------|
| 3D6 | gp 41,160 | (+) | 1 KAPPA | 8.65 | 3rd Nov., 1987 |
| 3D9 | gp 41,160 | (+) | 1 KAPPA | 8.0 | 2nd Feb., 1990 |
| 24G3 | gp 120,160 | (+) | 1 KAPPA | 8.5 | 17th Sep., 1990 |
| 25C2 | gp 120,160 | (+) | 1 KAPPA | 9.0 | 12th Dec., 1989 |
| 3A6 | p 24 | (+) | 1 KAPPA | 8.0 | 17th Sep., 1990 |
| 37G12 | p 55 | (+) | 1 KAPPA | 8.0 | 17th Sep., 1990 |
| 1H5 | gp 41,160 | (+) | 1 KAPPA | 8.0 | 17th Sep., 1990 |
| 1F11 | gp 41,160 | (+) | 1 KAPPA | 8.0 | 17th Sep., 1990 |
| 4D4 | gp 41,160 | (+) | 1 LAMDA | 8.5 | 17th Sep., 1990 |
| 2F5 | gp 41,160 | (+) | 3 KAPPA | n.d. | 17th Sep., 1990 |
| 4E10 | gp 41,160 | (+) | 3 KAPPA | 8.7 | 17th Sep., 1990 |
| 4G2 | gp 41,160 | (+) | 1 KAPPA | 8.0. | 17th Sep., 1990 |

*date of deposit at ECACC in Porton Down UK

Westernblots using commercial available strips (Du Pont) were determined as follows:

| Strip | | | |
|-------|------|----|-------|
| 1 | 3D6 | 13 | 3A6 |
| 2 | 25C2 | 14 | 3D9 |
| 3 | 1H5 | 17 | 4B3* |
| 4 | 24G3 | 22 | 4E10 |
| 5 | 1F11 | 23 | 2F5 |
| 6 | 4D4 | 25 | 37G12 |
| 10 | 4G2 | | |

About 300 ng/ml antibody were applied on each strip.

Cell line 2F5 and 4E10 have been deposited at the Public Health Laboratory Service, Center for Applied Microbiology and Research, Porton Down, Salisbury, Great Britian under deposit No. 90091704 and No. 90091703, respectively.

What we claim is:

1. An antibody produced by a cell line selected from the group consisting of cell line 2F5 having PHLS deposit No. 90.091704 and cell line 4E10 having PHLS deposit No. 90.091703.

2. A cell line selected from the group consisting of cell line 2F5 having PHLS deposit No. 90.091704 and cell line 4E10 having PHLS deposit No. 90.091703.

3. A human monoclonal antibody specifically binding to the envelope protein subunit gp41 of HIV-1 and having essentially the same binding characteristics as an antibody produced by a cell line defined in claim 2.

4. A human monoclonal antibody according to claim 3 being capable of preventing the infection of human cells by HIV-1 and the propagation of HIV-1 in vitro.

* * * * *